(12) United States Patent
Nakashima et al.

(10) Patent No.: US 11,969,487 B2
(45) Date of Patent: Apr. 30, 2024

(54) NON-CELLULAR ROOT CANAL FILLING MATERIAL AND NON-CELLULAR DENTAL TISSUE REGENERATION PROMOTING KIT

(71) Applicant: Kowa Company, Ltd., Aichi (JP)

(72) Inventors: Misako Nakashima, Aichi (JP); Koichiro Iohara, Aichi (JP)

(73) Assignee: Kowa Company, Ltd., Aichi (JP)

( * ) Notice: Subject to any disclaimer, the term of this patent is extended or adjusted under 35 U.S.C. 154(b) by 1070 days.

(21) Appl. No.: 16/651,483

(22) PCT Filed: Sep. 21, 2018

(86) PCT No.: PCT/JP2018/034948
§ 371 (c)(1),
(2) Date: Mar. 27, 2020

(87) PCT Pub. No.: WO2019/065478
PCT Pub. Date: Apr. 4, 2019

(65) Prior Publication Data
US 2020/0261321 A1 Aug. 20, 2020

(30) Foreign Application Priority Data
Sep. 29, 2017 (JP) ................. 2017-190744

(51) Int. Cl.
| | |
|---|---|
| A61K 6/54 | (2020.01) |
| A61K 35/35 | (2015.01) |
| A61K 38/19 | (2006.01) |
| A61K 38/48 | (2006.01) |
| A61K 39/395 | (2006.01) |
| A61K 47/64 | (2017.01) |
| A61L 27/36 | (2006.01) |
| A61L 27/38 | (2006.01) |
| A61L 27/40 | (2006.01) |
| A61P 1/02 | (2006.01) |

(52) U.S. Cl.
CPC .............. *A61K 6/54* (2020.01); *A61K 35/35* (2013.01); *A61K 38/19* (2013.01); *A61K 38/48* (2013.01); *A61K 38/4826* (2013.01); *A61K 39/395* (2013.01); *A61K 47/642* (2017.08); *A61L 27/36* (2013.01); *A61L 27/3865* (2013.01); *A61L 27/40* (2013.01); *A61P 1/02* (2018.01)

(58) Field of Classification Search
CPC ........ A61K 6/54; A61K 47/642; A61K 35/35; A61K 38/19; A61K 38/48; A61K 38/4826; A61K 39/395; A61P 1/02; A61L 27/36; A61L 27/3865; A61L 27/40
See application file for complete search history.

(56) References Cited

U.S. PATENT DOCUMENTS

| | | | | |
|---|---|---|---|---|
| 8,920,791 | B2* | 12/2014 | Nakashima | ............. A61P 43/00 424/93.7 |
| 10,668,134 | B2* | 6/2020 | Nakashima | ........... A61K 31/196 |
| 2011/0020310 | A1 | 1/2011 | Nakashima et al. | |
| 2011/0044960 | A1* | 2/2011 | Nakashima | ............. A61K 6/69 424/94.67 |
| 2012/0164604 | A1 | 6/2012 | Nakashima et al. | |
| 2014/0099605 | A1 | 4/2014 | Nakashima et al. | |
| 2014/0322672 | A1 | 10/2014 | Nakashima et al. | |
| 2019/0282675 | A1 | 9/2019 | Nakashima et al. | |

FOREIGN PATENT DOCUMENTS

| | | |
|---|---|---|
| JP | 5621105 | 11/2014 |
| JP | 5748194 | 7/2015 |
| JP | 5939559 | 6/2016 |
| JP | 6031658 | 11/2016 |
| WO | 2017/170996 | 10/2017 |

OTHER PUBLICATIONS

International Search Report and Written Opinion corresponding to International Application No. PCT/JP2018/034948 dated Dec. 18, 2018.
Goldberg et al. "Inflammatory and Immunological aspects of dental pulp repair", Pharmacol. Res. 58(2):137-147 (2008).
Hayashi et al. "Review of mechanism for recovering amount of dental pulp regeneration by means of continuous administration of anti-CCL11 antibody in elderly mouse", Regenerative Medicine 16:419 (2017).
Lin et al. "Transforming growth factor beta1 down-regulates Runx-2 and alkaline phosphatase activity of human dental pulp cells via ALK5/Smad2/3 signaling", Oral Surg Oral Med Oral Pathol Oral Radiol Endod 111:394-400 (2011).
Chang et al. "Role of ALK5/Smad2/3 and MEK1/ERK Signaling in Transforming Growth Factor Beta 1-modulated Growth, Collagen Turnover, and Differentiation of Stem Cells from Apical Papilla of Human Tooth", Journal of Endodontics 41(8):1272-1280 (2015).
Nakashima et al. "Pulp regeneration by transplantation of dental pulp stem cells in pulpitis: a pilot clinical study", Stem Cell Research and Therapy 8:61 (2017) (13 pages).

(Continued)

*Primary Examiner* — Michael P Cohen
(74) *Attorney, Agent, or Firm* — Myers Bigel, P.A.

(57) ABSTRACT

A non-cellular dental tissue regeneration promoting kit is provided that makes effective dental tissue regeneration possible without transplantation of autologous or allogeneic stem cells or components derived from stem cells. The kit comprises: a pretreatment agent comprising a serine protease; and a non-cellular root canal filling material, the non-cellular root canal filling material comprising: a regeneration promoting compound including at least one of a CCR3 antagonist, a CCL11 neutralizing antibody, and an ALK5 inhibitor; and an extracellular matrix. The kit is preferably used for middle-aged or elderly individuals.

10 Claims, 10 Drawing Sheets

Specification includes a Sequence Listing.

(56) References Cited

OTHER PUBLICATIONS

Galler "Clinical procedures for revitalization: current knowledge and considerations", International Endodontic Journal 49:926-936 (2016).
Kontakiotis et al. "Regenerative Endodontic Therapy: A Data Analysis of Clinical Protocols", J Endod 41(2):146-154 (2015).
Del Fabbro et al. "Autologous Platelet Concentrates for Pulp and Dentin Regeneration: A Literature Review of Animal Studies", J Endod 42(2):250-257 (2016).
Yang et al. "Pulp Regeneration: Current Approaches and Future Challenges", Frontiers in Physiology vol. 7, Article 58 (2016 (9 pages).
He et al. "Regenerative Endodontics for Adult Patients", J Endod 43(95):557-564 (2017).
Iohara et al. "A Novel Combinatorial Therapy with Pulp Stem Cells and Granulocyte Colony-Stimulating Factor for Total Pulp Regeneration", Stem Cells Translational Medicine 2:521-533 (2013).
Cao et al. "Pulp-dentin Regeneration: Current State and Future Prospects", Journal of Dental Research 94(11):1544-1551 (2015).
Noguchi et al. "Clinical Studies on the Enzyme Tryfsin, Especially on the Histochemical Significance of Enzymatic Debridement of the Necrotic Skin Lesion", Japanese Journal of Dermatology and Venerology 64:497-506 (1954).
Kawamura et al. "EDTA soluble chemical components and the conditioned medium from mobilized dental pulp stem cells contain an inductive microenvironment, promoting cell proliferation, migration, and odontoblastic differentiation", Stem Cell Research & Therapy 7:77 (2016) (14 pages).

\* cited by examiner

SEQUENCE LISTING

<160> NUMBER OF SEQ ID NOS: 6

<210> SEQ ID NO 1
<211> LENGTH: 20
<212> TYPE: DNA
<213> ORGANISM: Artificial
<220> FEATURE:
<223> OTHER INFORMATION: primer

<400> SEQUENCE: 1
ggacttcgag caagagatgg          20

<210> SEQ ID NO 2
<211> LENGTH: 20
<212> TYPE: DNA
<213> ORGANISM: Artificial
<220> FEATURE:
<223> OTHER INFORMATION: primer

<400> SEQUENCE: 2
agcactgtgt tggcgtacag          20

<210> SEQ ID NO 3
<211> LENGTH: 21
<212> TYPE: DNA

```
<213> ORGANISM: Artificial
<220> FEATURE:
<223> OTHER INFORMATION: primer

<400> SEQUENCE: 3
ttctgtggct gctgctcata g                                            21

<210> SEQ ID NO 4
<211> LENGTH: 20
<212> TYPE: DNA
<213> ORGANISM: Artificial
<220> FEATURE:
<223> OTHER INFORMATION: primer

<400> SEQUENCE: 4
gctctctagt cgctgaaggg                                              20

<210> SEQ ID NO 5
<211> LENGTH: 22
<212> TYPE: DNA
<213> ORGANISM: Artificial
<220> FEATURE:
<223> OTHER INFORMATION: primer

<400> SEQUENCE: 5
ctgtactccc tggtgttcac tg                                           22

<210> SEQ ID NO 6
<211> LENGTH: 21
<212> TYPE: DNA
<213> ORGANISM: Artificial
<220> FEATURE:
<223> OTHER INFORMATION: primer

<400> SEQUENCE: 6
ggttgagcag gtagatgttg g                                            21
```

NON-CELLULAR ROOT CANAL FILLING MATERIAL AND NON-CELLULAR DENTAL TISSUE REGENERATION PROMOTING KIT

RELATED APPLICATIONS

This application is a 35 U.S.C. § 371 national phase application of PCT Application PCT/JP2018/034948 filed Sep. 21, 2018, which claims priority to Japanese Application No. 2017-190744 filed Sep. 29, 2017. The entire contents of each are incorporated herein by reference in its entirety.

STATEMENT REGARDING ELECTRONIC FILING OF A SEQUENCE LISTING

A Sequence Listing in ASCII text format, submitted under 37 C.F.R. § 1.821, entitled 5576-367_ST25.txt, 1,438 bytes in size, generated on Mar. 24, 2020, and filed via EFS-Web, is provided in lieu of a paper copy. This Sequence Listing is hereby incorporated by reference into the specification for its disclosures.

FIELD OF THE INVENTION

The present invention relates to non-cellular root canal filling materials and to non-cellular dental tissue regeneration promoting kits that promote regeneration of dental pulp, dentin, and periapical tissue without using stem cells or stem cell components.

BACKGROUND OF THE INVENTION

Dental health and the ability to bite well are important for healthy ageing in the super-ageing society. However, over 20% of middle-aged and elderly people have a disease (infected root canal) in which the removal of a dental pulp (pulpectomy) has been performed and the treated tooth is re-infected several decades later and tissue under the root festers. Furthermore, about 25% of them are not completely cured even after treatment. The chronic infective lesion has an extensive systemic effect on elderly people with weakened immune systems. Many elderly people are on medication with a therapeutic agent for osteoporosis, and tooth extraction is not appropriate for them. Moreover, even if tooth extraction is conducted, the number of cases to which an implant is appropriate is reduced in middle-aged and elderly people.

Meanwhile, tooth loss leads to impairment of dental occlusion, articulation, taste, the sense of touch, and/or aesthetics, and/or the reduction of QOL. Recently, there are concerns that oral frailty due to the reduction of tooth and oral function may lead to sarcopenia such as muscle weakness and declining body function and/or declining functioning due to undernutrition or the like and results in a condition requiring long-term care.

Accordingly, for the maintenance of tooth and oral functions, dental pulp regeneration therapies have been developed in which dental pulp stem cells taken from an unnecessary autologous tooth is autologously transplanted or dental pulp stem cells taken from an unnecessary tooth of others are allogeneically transplanted to restore the tooth to its original state so as to avoid an infected root canal and tooth extraction after the pulpectomy (Patent Documents 1 to 3). Moreover, the dental pulp is regenerated by autologous or allogeneic transplantation of not only dental pulp stein cells but also other tissue stem cells derived from bone marrow or adipose tissue.

However, such therapies are inferior to dental pulp stem cell transplantation in the amount of dental pulp regeneration, the amount of angiogenesis, and the amount of nerve regeneration (Patent Document 4). The safety of the dental pulp regeneration therapies involving autologous dental pulp stem cell transplantation has already been confirmed by clinical studies and their efficacy has been suggested (Non-Patent Document 1).

Meanwhile, an alternative to the stem cell therapies in the dental pulp regeneration therapies is cell homing. For teeth with incomplete root formation in young humans, a method involving filling a blood clot in the root canal without using dental pulp stem cells is mainstream (Non-Patent Document 2). Alternatives include a method involving injecting platelet-rich plasma (PRP) instead of a blood clot (Non-Patent Document 3).

However, it is known that the regeneration of dental pulp-specific tissue is little formation found, and only fibrous or bone-like tissue mainly rich in blood vessels is regenerated (Non-Patent Document 4). In animal experiments, cell homing methods without stem cells in which a growth factor or a cytokine such as stromal cell derived factor (SDF1α), basic fibroblast growth factor (bFGF), platelet-derived growth factor (PDGF), stem cell factor (SCF), and granulocyte colony-stimulating factor (G-CSF) is used as a migration factor has been developed (Non-Patent Document 5).

However, it has been reported that a sufficient amount of regenerated dental pulp is not achieved, but most are considerably dense fibrous connective tissue with blood vessels and the entire root canal may be calcified (Non-Patent Documents 6, 7). Accordingly, stem cells have so far been considered to be essential for pulp tissue regeneration, particularly in teeth with complete root formation (Patent Document 8).

However, autologous stem cell transplantation has drawbacks that an unnecessary autologous tooth such as a wisdom tooth is necessary when dental pulp stem cells are used, the confirmation of safety of cell processing products is expensive, that cells cannot be immediately supplied when they are required, and that, in middle-aged and elderly people, traits of stem cells change, the total number of dental pulp stem cells that can be taken decreases, and proliferation takes time. In the allotransplantation, the cost required for the confirmation of safety after the production of the cells is decreased in comparison with the autologous transplantation due to the increase of the number of cell products per lot, but there remain unsolved issues such as the issue of a source of teeth whose safety is secured, legal issues such as rights of and rewards to human donors of teeth upon commercialization of human dental pulp stein cell products, and the issue of safety of immune responses in humans.

Accordingly, development of a technique that promotes regeneration of dental tissue after the pulpectomy or the treatment of an infected root canal, more specifically, dental pulp, dentin, and periapical tissue without using stem cells or components derived from stem cells is desired. Meanwhile, it is considered that appropriate signal factors can be selected by further studies of stem cell sources that promote migration of host cells used for dental pulp regeneration. More specifically, future development of the dental pulp regeneration with appropriate signal factors that promote the migration of host stem cells having angiogenic potential and nerve differentiation potency and suppress the migration of cells having osteogenic and cementogenic capacities is desired (Non-Patent Document 9).

Among them, the regeneration of dental pulp in middle-aged and elderly individuals is slower than that in young individuals. Recently, in canine animal experiments of in dental pulp regeneration therapies regeneration of dental pulp has been promoted when a CCL11-neutralizing antibody/CCR3 antagonist or an ALK5 inhibitor is transplanted with dental pulp stem cells of in dental pulp regeneration therapies middle-aged and elderly individuals. Alternatively, dental pulp regeneration was promoted when root canals of teeth in middle-aged and elderly individuals are pretreated with trypsin before the dental pulp stem cell transplantation (Patent Document 5). The CCL11 neutralizing antibody or CCR3 antagonist inhibits the binding of CCL11 to CCR3 and blocks the signal transduction. Moreover, GDF11 binds to type I TGF-beta superfamily receptors ACVR1B (ALK4), TGFBR1 (ALK5) and ACVR1C (ALK7) and the signal is transmitted by ALK4 and ALK5. The ALK5 inhibitor blocks the signal transduction by GDF11. It is considered that at the time of the dental pulp regeneration, secreted factors from dental pulp stem cells accumulated in dentin are released from the dentin to promote the dental pulp regeneration (Non-Patent Document 10). Adding a CCR3 antagonist to culture supernatant containing secreted factors from senescent dental pulp stem cells in vitro significantly increased the neurite extension promoting activity and the migration promoting activity of the culture supernatant. Moreover, adding an ALK5 inhibitor significantly increased the blood vessel-inducing capability and the neurite extension promoting activity of culture supernatant. Accordingly, it has been suggested that the dental pulp regeneration-promoting activity of the CCR3 antagonist or the ALK5 inhibitor in middle-aged and elderly dogs is based on the blood vessel induction-promoting, neurite extension promoting, and migration promoting activities.

However, no effect of the transplantation of the CCR3 antagonist or ALK5 inhibitor with dental pulp stem cells on the dental pulp regeneration in young dogs was observed (Patent Document 5). Meanwhile, trypsin is used for the purpose of lysing necrotic tissue, blood clots, and/or denatured protein as a pharmaceutical preparation and making a wounded surface normal to facilitate the action of antibiotics (Non-Patent Document 11). Seeding dental pulp stem cells on dentin surfaces treated with trypsin in vitro increased the adhesion of the cells and promotion of differentiation into odontoblasts was observed.

Accordingly, it has been suggested that the dental pulp regeneration promoting activity upon trypsin pretreatment in middle-aged and elderly dogs is based on the inactivation of an inhibitor accumulated in middle-aged or elderly dentin by proteolytic activity or the activation of the precursor by cleavage, the promotion of adhesion of cells to dentin, and the odontoblast differentiation promoting activity.

However, no effect of the trypsin pretreatment on the dental pulp regeneration in young dogs was observed (Patent Document 5). Moreover, dental pulp regeneration was hardly observed when only the trypsin pretreatment but no transplantation of dental pulp stem cells is provided, or when only the CCR3 antagonist or ALK5 inhibitor but no dental pulp stem cells is transplanted (Patent Document 5).

CITATION LIST

Patent Document

[Patent Document 1] JP 5621105 B
[Patent Document 2] JP 6031658 B
[Patent Document 3] JP 5748194 B
[Patent Document 4] JP 5939559 B
[Patent Document 5] Japanese Patent Application No, 2016-072306, PCT/JP2017/13572

Non-Patent Document

[Non-Patent Document 1] Nakashima M., Iohara K., Murakami M., Nakamura H., Sato Y., Ariji Y., Matsushita K.: Pulp regeneration by transplantation of dental pulp stem cells in pulpitis: A pilot clinical study. Stem Cell Res Therapy. 8 (1): 61, 2017.
[Non-Patent Document 2] Galler K M.: Clinical procedures for revitalization: current knowledge and considerations. Int Endod J. 2016 October; 49(10): 926-36.
[Non-Patent Document 3] Kontakiotis E G, Filippatos C G, Tzanetakis G N, Agrafioti A.: Regenerative endodontic therapy: a data analysis of clinical protocols. J Endod. 41 (2): 146-54. 2015.
[Non-Patent Document 4] Del Fabbro M, Lolato A, Bucchi C, Taschieri S, Weinstein R L.: Autologous platelet concentrates for pulp and dentin regeneration: a literature review of animal studies. J Endod. 42 (2): 250-7, 2016.
[Non-Patent Document 5] Yang J., Yuan G., Chen Z.: Pulp Regeneration: Current Approaches and Future Challenges. Front Physiol.: 7: 58, 2016.
[Non-Patent Document 6] He L, Kim S G, Gong Q, Zhong J, Wang S, Zhou X, Ye L, Ling J, Mao J J.: Regenerative endodontics for adult patients. J Endod. 43(9S):S57-S64, 2017.
[Non-Patent Document 7] Iohara K, Murakami M, Takeuchi N, Osako Y, Ito M, Ishizaka R, Utunomiya S, Nakamura H, Matsushita K, Nakashima M.: A novel combinatorial therapy with pulp stem cells and granulocyte colony-stimulating factor for total pulp regeneration. Stem Cells Transl. Med. 2 (7): 521-533, 2013.
[Non-Patent Document 8] Cao Y, Song M, Kim E, Shon W, Chugal N, Bogen G, Lin L, Kim R H, Park N H, Kang M K. Pulp-dentin Regeneration: Current State and Future Prospects. J Dent Res. 94 (11): 1544-51, 2015.
[Non-Patent Document 9] Yang J, Yuan G, Chen Z.: Pulp Regeneration: Current Approaches and Future Challenges. Front Physiol. 7: 58, 2016. eCollection 2016.
[Non-Patent Document 10] Kawamura R, Hayashi Y, Murakami H, Nakashima M.: EDTA soluble chemical components and the conditioned medium from mobilized dental pulp stem cells contain an inductive microenvironment, promoting cell proliferation, migration and odontoblastic differentiation. Stem Cell Res. Ther. 7 (1): 77, 2016.
[Non-Patent Document 11] Japanese journal of dermatology and venereology, vol. 64, Noguchi Yoshikuni, et al., p. 497-506, 1954

SUMMARY OF INVENTION

Technical Problem

The present invention was made in view of such issues and an object of the present invention is to provide a non-cellular root canal filling material that makes effective dental tissue regeneration possible, non-cellularly, particularly without transplantation of autologous or allogeneic stem cells or components derived from stem cells, in dental tissue regeneration. Another object of the present invention is to provide a non-cellular dental tissue regeneration promoting kit involving the non-cellular root canal filling material.

Solution to Problem

The non-cellular root canal filling materials for dental tissue regeneration according to the present invention comprise: a regeneration promoting compound including at least any one of a CCR3 antagonist, a CCL11 neutralizing antibody, and an ALK5 inhibitor; and an extracellular matrix. The non-cellular root canal filling materials may include at least one migration factor such as G-CSF, bFGF, and SDF-1.

The non-cellular dental tissue regeneration promoting kits for dental tissue regeneration according to the present invention comprise: a pretreatment agent comprising a serine protease; a regeneration promoting compound including at least any one of a CCR3 antagonist, a CCL11 neutralizing antibody, and an ALK5 inhibitor; and an extracellular matrix. The non-cellular dental tissue regeneration promoting kit may include at least one migration factor such as G-CSF, bFGF, and SDF-1.

Advantageous Effects of Invention

According to the present invention, dental tissue regeneration can be effectively provided without transplantation of autologous or allogeneic dental pulp stem cells or components (supernatant, secretome, or exosome) derived from such stem cells.

DESCRIPTION OF EMBODIMENTS

Figure 1:
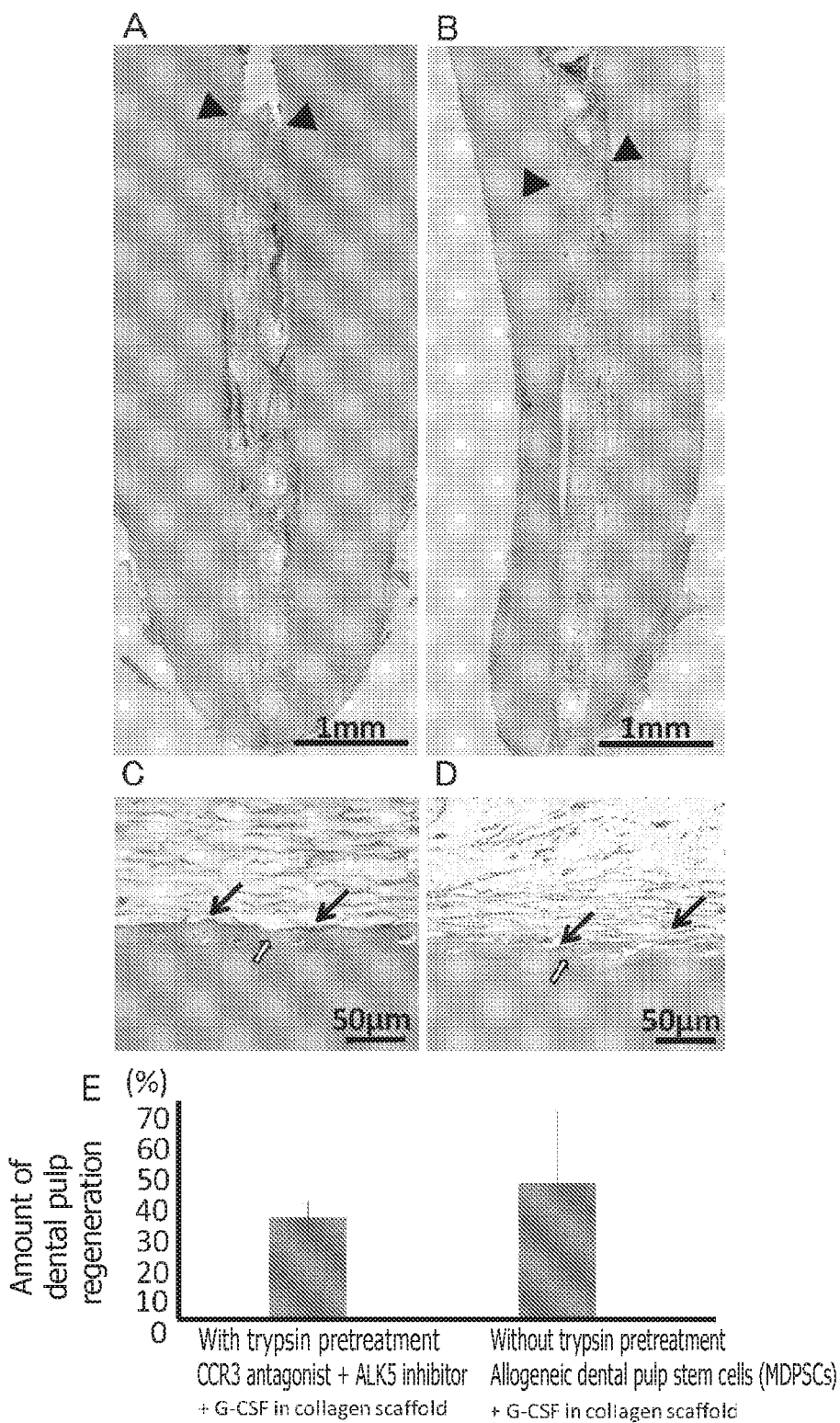
FIG. 1 is a set of photographs of H-E staining of regenerated dental pulp tissue after 28 days of transplantation by a non-cellular dental tissue regeneration promoting kit or regenerated dental pulp tissue by a conventional cellular root canal filling material in 2-year-old dogs. A and B are at low magnification and the arrow heads indicate the top of regenerated tissue. C and D are at high magnification, and the black arrows indicate odontoblast-like cells and the white arrows indicate the formation of dentin-like hard tissue. Among them, A and C illustrate regenerated dental pulp tissue after treatment with a pretreatment agent comprising trypsin for 10 minutes and transplantation of the non-cellular root canal filling material in which regeneration promoting compounds (CCR3 antagonist, ALK5 inhibitor) is mixed with atelocollagen and the migration factor G-CSF. B and D illustrate regenerated dental pulp tissue after transplantation of the cellular root canal filling material in which allogeneic dental pulp stem cells (MDPSCs) and the migration factor G-CSF are mixed with atelocollagen without pretreatment. E illustrates statistical analysis of the amount of dental pulp regeneration.

Referring to the accompanying drawings, embodiments of the present invention will specifically be described below.

The embodiments are provided to facilitate the understanding of the principle of the present invention and the scope of the present invention is not limited to the following embodiments and other embodiments whose configurations are modified as needed from those of the following embodiments by one skilled in the art are also encompassed within the scope of the present invention.

Non-cellular root canal filling materials for dental tissue regeneration according to the present embodiment comprise: a regeneration promoting compound including at least any one of a CCR3 antagonist, a CCL11 neutralizing antibody, and an ALK5 inhibitor; and an extracellular matrix. The non-cellular root canal filling materials may include at least one migration factor such as G-CSF, bFGF, and SDF-1.

Non-cellular dental tissue regeneration promoting kits for dental tissue regeneration according to the present invention comprise: a pretreatment agent comprising a serine protease; a regeneration promoting compound including at least any one of a CCR3 antagonist, a CCL11 neutralizing antibody, and an ALK5 inhibitor; and an extracellular matrix. The non-cellular dental tissue regeneration promoting kits may include at least one migration factor such as G-CSF, bFGF, and SDF-1.

The dental tissue regeneration is regeneration of tissue including at least one of dental pulp, dentin, and periapical tissue.

While both the ALK5 inhibitor and the CCR3 antagonist or CCL11 neutralizing antibody are effective in dental pulp regeneration, the ALK5 inhibitor, on one hand, is more effective than the CCR3 antagonist or CCL11 neutralizing antibody in angiogenesis and the CCR3 antagonist or CCL11 neutralizing antibody, on the other hand, is more effective than the ALK5 inhibitor in neuropoiesis. When a mixture of the ALK5 inhibitor and the CCR3 antagonist or CCL11 neutralizing antibody is used, the mixing ratio is not particularly limited, but examples thereof may include 10% by weight:90% by weight to 90% by weight:10% by weight.

The ALK5 inhibitor is not particularly limited, but examples thereof include the following compounds.

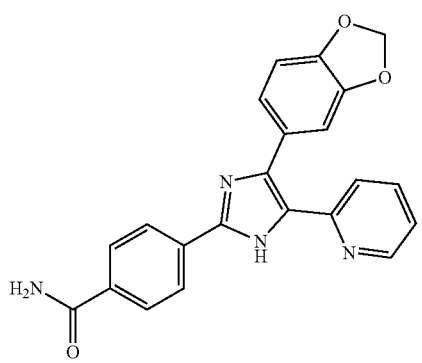

[Formula 1]

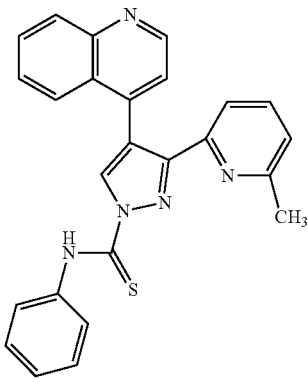

[Formula 2]

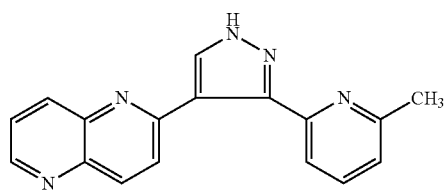

[Formula 3]

Moreover, the CCR3 antagonist is not particularly limited, but examples thereof include the following compounds.

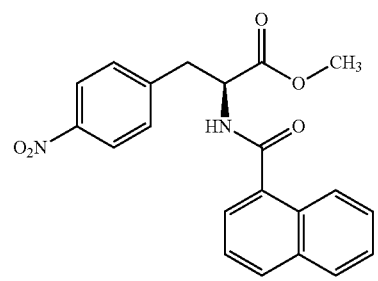

[Formula 4]

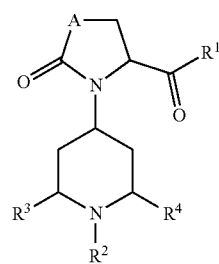

[Formula 5]

In the formulas, A is $CH_2$ or O, $R^1$ is NHR (wherein R is C1-C6 alkyl), $R^2$ is C1-C6 alkylene-phenyl, $R^3$ is H or C1-C6 alkyl, and $R^4$ is H or C1-C6 alkyl.

While the signal of CCL11 is transmitted via CCR3 as a receptor, the anti-CCL11 neutralizing antibody binds to CCL11, serving to inhibit the binding of CCL11 to CCR3 and suppressing the signal transduction of CCL11. Meanwhile, the CCR3 antagonist also binds to the receptor CCR3 and similarly serves to inhibit the binding of CCL11 to CCR3. The anti-CCL11 neutralizing antibody to be used may be an antibody commercially available.

The CCL11 neutralizing antibody or CCR3 antagonist that suppresses CCL11 or the ALK5 inhibitor that inhibits the signal transduction of GDF11 according to the present embodiment is for example, at 50 ng/ml to 50 µg/ml and preferably at 3 µg/ml to 30 µg/ml.

The extracellular matrix is not particularly limited, but examples thereof include at least one of collagen, artificial proteoglycan, gelatin, hydrogel, fibrin, phosphophoryn, heparan sulfate, heparin, laminin, fibronectin, alginic acid, hyaluronic acid, chitin, chitosan, PLA, PLGA, PEG, PGA, PDLLA, PCL, hydroxyapatite, β-TCP, calcium carbonate, titanium, and gold.

The non-cellular root canal filling materials may include a migration factor. The migration factor, for example, includes at least any one of G-CSF, SDF-1, bFGF, TGF-beta, NGF, PDGF, BDNF, GDNF, EGF, VEGF, SCF, MMP3, Slit, GM-CSF, LIF, and HGF. The migration factor is added for the purpose of promoting the migration capacity of host stem cells around teeth or the like, which declines with age. The migration factor is preferably G-CSF or bFGF or SDF-1.

The non-cellular root canal filling materials according to the present embodiment are preferably used in young individuals, but may also be applied to middle-aged and elderly individuals. The young individuals are not particularly limited, but examples thereof are those at the age of 1 year or older and 29 years or younger for humans, at the age of 1 week or older and 29 weeks or younger after birth for rats, and at the age of 1 week or older and 1 year or younger after birth for dogs.

The non-cellular dental tissue regeneration promoting kits according to the present embodiment comprise: a pretreatment agent comprising a serine protease; and the non-cellular root canal filling material described above.

The pretreatment agent is used before inserting a non-cellular root canal filling material in a root canal. The pretreatment refers to injecting a liquid containing a serine protease into a root canal. By using the pretreatment agent, a treatment by which inhibitors that suppress tissue regeneration in teeth and periodontal tissue are degraded or one or more migration factors are activated or changed from a latent form to an active form can be provided.

The serine protease is a protease (proteolytic enzyme) having a serine residue involved in the nucleophilic attack as a catalytic residue. Serine proteases are classified into subtilisin-like serine proteases and chymotrypsin-like serine proteases based on the similarity of amino acid sequences and conformations. The former includes subtilisin BPN', thermitase, proteinase K, lantibiotic peptidase, kexin, cucumisin, and the like and the latter includes trypsin, chymotrypsin, thrombin, factor Xa, elastase, and the like. The serine protease is preferably a chymotrypsin-like serine protease and more preferably trypsin.

The concentration of the serine protease included in the pretreatment agent is not particularly limited as long as it is a concentration at which a treatment by which inhibitors that suppress tissue regeneration in teeth and periodontal tissue are degraded or a migration factor is activated can be provided, but it is, for example, 10 µg/ml (0.001%) to 50 mg/ml (5%) and preferably 500 µg/ml (0.05%) to 5 mg/ml (0.5%).

The duration of the injection of the pretreatment agent into a root canal is not particularly limited as long as it is sufficient to provide a treatment by which inhibitors that suppress tissue regeneration in teeth and periodontal tissue are degraded or a migration factor is activated, but it is, for example, from 3 to 30 minutes, preferably from 5 to 20 minutes, and more preferably 10 minutes.

The pretreatment agent according to the present embodiment may include nanobubbles in addition to the serine protease. The nanobubbles comprise vesicles formed of lipid and a gas or a gas precursor filling the vesicles. The diameter of the nanobubbles is not particularly limited, but is, for example, 10 to 500 nm and preferably 70 to 300 nm. The diameter of nanobubbles is, for example, measured with a nanoparticle size distribution analyzer (SALD-7100, Shimadzu Corporation). The lipid composition, the charge state, the density, the weight, the particle size, and the like of the nanobubbles may be designed as appropriate. The lipid used for preparing the vesicles is not particularly limited, but is composed of membrane components containing lipid. Examples of the lipid are phospholipid, glycoglycerolipid, and sphingoglycolipid as well as cationic lipids composed of these lipids and a primary amino group, a secondary amino group, a tertiary amino group, or a quaternary ammonium group introduced therein.

When the nanobubbles are contained in the pretreatment agent, the nanobubble concentration is expressed by the number of the nanobubbles in the pretreatment agent. The nanobubble concentration is not particularly limited, but may be, for example, $2 \times 10^7$ per cm$^3$ to $2 \times 10^9$ per cm$^3$. The nanobubble concentration can be quantitatively analyzed, for example, by electron spin resonance spectroscopy (ESR).

The non-cellular dental tissue regeneration promoting kits according to the present embodiment are preferably used in middle-aged and elderly individuals. The middle-aged individuals are not particularly limited, but are, for example, those at the age of 30 years or older and 49 years or younger for humans, at the age of 30 weeks or older and 39 weeks or younger after birth for rats, and at the age of 2 years or older and 4 years or younger after birth for dogs. The elderly individuals are not particularly limited, but are, for example, those at the age of 50 years or older for humans, at the age of 40 weeks after birth or older for rats, and at the age of 5 years after birth or older for dogs. Therefore, herein, the human middle-aged or elderly individual is defined to be an individual at the age of 30 years or older, the rat middle-aged or elderly individual is defined to be an individual at the age of 30 weeks after birth or older, and the dog middle-aged or elderly individual is defined to be an individual at the age of 2 years after birth or older.

EXAMPLES

Example 1

Membrane-Fractionated Dog Allogeneic Dental Pulp Stem Cells

Young dogs were given general anesthesia and then maxillary canine teeth were extracted. A cleavage line of a degree not to reach the dental pulp was made from the tooth crown to the tooth root part in the lengthwise direction with a turbine bur. The teeth were transported in Hanks' solution containing 20 µg/ml gentamicin (Gentalol (R), Nitten Pharmaceutical Co., Ltd) and 0.25 µg/ml amphotericin B (Fungizone (R), Bristol-Myers Company) as transport solution using a special transportation container under temperature control within 1 hour. The dental pulp was extracted and cut on a clean bench and 5 ml of 0.04 mg/ml Liberase solution was added thereto. After mixing by inversion, the mixture was shaken on Thermomixer comfort (Eppendorf AG) at 37° C., 500 rpm for 30 minutes. After the shaking, the mixture was suspended 30 times and centrifuged at 200 rpm for 1 minute. The supernatant in the centrifugal tubes was collected and this supernatant was centrifuged at 2,000 rpm for 5 minutes. DMEM containing 10% canine serum was added to precipitated cells and the cells were suspended. The suspension was then centrifuged at 2,000 rpm for 5 minutes. 5 ml of DMEM containing 10% canine serum was added to reprecipitated cells and the cells were suspended 30 times. The cell suspension was mixed with an equal amount of trypan blue (0.4%, SIGMA) and the mixture was suspended 10 times and the number of living cells was counted. The remaining suspension was homogeneously seeded into a T25 flask and then cultured in a $CO_2$ incubator (Panasonic Corporation, 37° C., $CO_2$ 5%) and the morphology was observed. The cells were subcultured after reaching a confluency of 60 to 70%. Subsequently, in the second generation, mobilized dental pulp stem cells were fractionated by stem cell membrane fractionation. More specifically, the cells were seeded on the top of a membrane at $2 \times 10^4$ cells/100 µl and the migration factor G-CSF (Neutrogin, Chugai Pharmaceutical Co., Ltd) was added at a final concentration of 100 ng/ml into DMEM containing 10% autologous canine serum in wells of a 24-well plate, the lower structure. The G-CSF was removed 48 hours later and the medium was changed to DMEM containing 10% autologous canine serum. The cells were further cultured, subcultured after a confluency of 70%, repeated subculture to the sixth generation, and frozen.

For cell surface antigens, cells in the seventh generation were seeded at $1 \times 10^7$ cells/ml in PBS containing 20% serum, subjected to blocking (FcγIII/II receptor blocking) at 4° C. for 20 minutes, and examined about the stem cell surface markers (CD31 (PE) (JC70A) (Dako), CD29 (PE-Cy7) (HMb1-1) (eBioscience), CD44 (Phycoerythrin-Cy7, PE-Cy7) (IM7) (eBioscience), CD73 (APC) (AD2) (BioLegend), CD90(PE) (YKIX337.217) (eBioscience), CD105 (PE) (43A3) (BioLegend), and CXCR4 (FITC) (12G5) (R & D)) for 90 minutes at 4° C. in dark. As negative controls, mouse IgG1 negative control (AbD Serotec), mouse IgG1 negative control (fluorescein isothiocyanate, FITC) (MCA928F) (AbD Serotec), mouse IgG1 negative control (Phycoerythrin-Cy7, PE-Cy7) (299Arm) (eBioscience) were used. The positive rate was compared with a flow cytometer (FACS Aria II (BD bioscience)).

The cryopreserved sixth generation cells were thawed. Examination of the expression of the surface antigens by flow cytometry revealed that the positive rates of CD29, CD44, CD73, CD90, and CD105 were 95% or higher and that CD31 was negative. From this, it was considered that many stem cells and/or progenitor cells were included. Moreover, the CXCR4-positive rate was about 18%.

As for dog mobilized dental pulp stem cells, it has been found that there is no difference seen qualitatively or quantitatively in dental pulp regeneration between when allogeneic cells are transplanted into a root canal without matching the haplotype of DLAs (dog leukocyte antigens, dog major histocompatibility antigens) and when the transplantation is performed with matching the haplotype.

Comparison of Dental Pulp Regeneration Using Non-Cellular Dental Tissue Regeneration Promoting Kit: Stem Cell Therapy After Pulpectomy in Middle-Aged Dogs)

After giving general anesthesia, the pulpectomy of maxillary and mandibular anterior teeth in middle-aged (2-year-old) dogs was performed. The pulpectomy were performed to the apical area with #50 to 55, then washed alternately with 5% sodium hypochlorite solution and with 3% hydrogen peroxide solution, and further washed with saline. The root canals were completely dried with a paper point and sealed with temporarily cement and resin completely after stopping the bleeding. Then, 4 days after the pulpectomy, the temporary seals were removed and the openings were rewashed alternately and washed with saline. The root canals were then treated with 3% EDTA (Smear clean, Nippon Shika Yakuhin Co., Ltd.) for 2 minutes, further washed with saline, and dried. Subsequently, the right root canals were treated with a 500 µg/ml (0.05%, dissolved in nanobubble water) trypsin preparation (Francetin T powder (2,500 USP crystal trypsin per 10 mg), Mochida Pharmaceutical Co., Ltd.) for 10 minutes to be pretreated and washed with saline. Subsequently, the root canals were filled with a non-cellular root canal filling material comprising 200 ng of a CCR3 antagonist (SB328437, TOCRIS bioscience) and 200 ng of an ALK5 inhibitor (SB431542, TOCRIS bioscience) as regeneration promoting compounds, 150 ng of the migration factor G-CSF (Neutrogin, Chugai Pharmaceutical Co., Ltd.), and 20 µl of the extracellular matrix collagen (Koken atelocollagen implant, Koken Co., Ltd.). As a control, the left root canals were not pretreated with trypsin in the root canal and $5 \times 10^5$ membrane-fractionated allogeneic dental pulp stem cells were suspended into 20 µl of collagen. Then, 150 ng of G-CSF (Neutrogin) was further added to prepare a root canal filling material (cellular root canal filling material) and this root canal filling material was injected with care not to form air bubbles in the root canal. The membrane-fractionated dental pulp stem cells were dental pulp stem cells fractionated with a membrane fractionation incubator described above. Subsequently, a gelatin sponge (Spongel, Astellas Pharma Inc.) for hemostasis was placed thereon and the cavities were completely sealed with a glass ionomer cement (GC Fuji IX EXTRA, GC) and a photo-polymerized resin (Clearfil Mega Bond and Clearfil DC core automix, Kuraray Noritake Dental Inc.). The teeth were extracted 28 days after the transplantation and 5 µm paraffin pieces on longitudinal sections were prepared according to a usual method and the morphology was observed after the H-E staining. The amount of regenerated dental pulp in each specimen (n=3) was expressed as the mean of 3 samples with 4 sections per sample measured. The angiogenesis was examined by comparison of immunostaining of Day 30 specimens with 20 µg/ml Fluorescence Griffonia (Bandeiraea) Simplicifolia Lectin 1/fluorescein-Galanthus nivalis (snowdrop) lectin, BS-1 lectin, Vector lab.) for 15 minutes. The neurite extension was examined by comparison of immunostaining of Day 28 specimens with PGP9.5 (Ultra Clone, 1:10,000). Furthermore, to confirm the differentiation into dental pulp and odontoblasts, respectively immunostaining with the dental pulp marker TRH-DE (Thyrotropin-releasing hormone-degrading ectoenzyme) and in situ hybridization of the odontoblast marker enamelysin of Day 28 specimens were performed (see Iohara, et al., 2011, Tissue Engineering part A). The color development of the TRH-DE immunostaining was performed with DAB (VECTASTAIN ABC kit, Vector lab.) using a primary antibody (anti-canine TRH-DE, mouse IgM clone #6E5E, 1:100, MBL) and a secondary antibody (Goat anti-mouse IgM, poly-biotin, 1:50, Vector).

Figure 2:
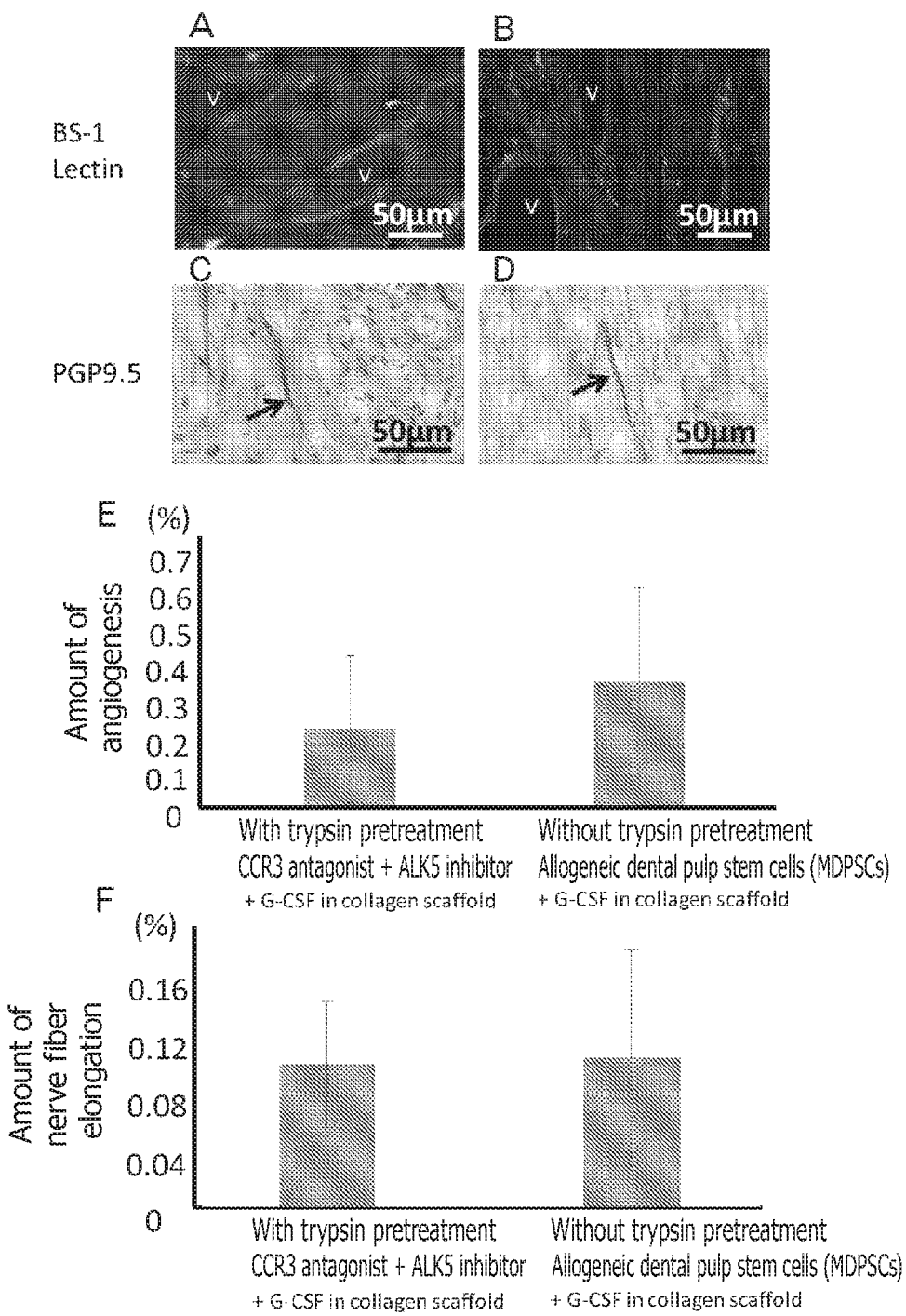
FIG. 2 is a set of photographs on Day 28 after transplantation illustrating the comparison of the angiogenesis and the neurite extension in tissue regenerated with a non-cellular dental tissue regeneration promoting kit and with a conventional cellular root canal filling material in 2-year-old dogs. A and B illustrate angiogenesis (BS-1 lectin staining) and V indicates neovessels. C and D illustrate the neurite extension (PGP9.5 staining) and the arrows indicate neurites. Among them, A and C illustrate regenerated tissue after treatment with a pretreatment agent comprising trypsin for 10 minutes and transplantation of the non-cellular root canal filling material in which a CCR3 antagonist, an ALK5 inhibitor, and G-CSF is mixed with atelocollagen. B and D illustrate regenerated tissue after transplantation of the cellular root canal filling material in which allogeneic dental pulp stem cells (MDPSCs) and G-CSF are mixed with atelocollagen without pretreatment. E illustrates statistical analysis of amount of angiogenesis. F illustrates statistical analysis of amount of neurite extension.
Figure 3:
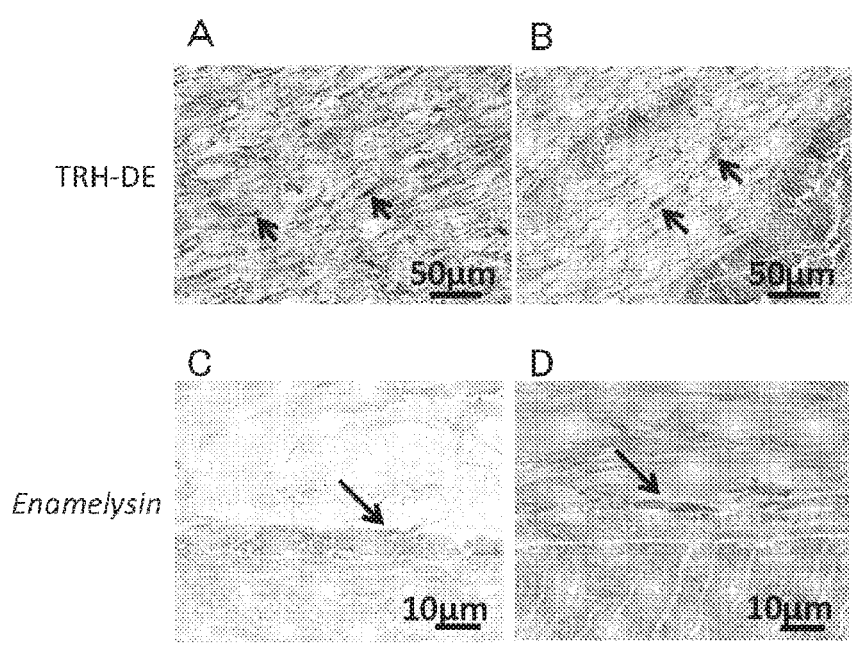
FIG. 3 is a set of photographs of regenerated tissue on Day 28 after transplantation using dental pulp and odontoblast markers in 2-year-old dogs. A and B illustrate a dental pulp marker (TRH-DE immunostaining) and the arrows indicate positive cells. C and D illustrate in situ hybridization of the odontoblast marker Enamelysin mRNA and the arrows indicate positive cells. Among them, A and C illustrate regenerated tissue after treatment with a pretreatment agent comprising trypsin for 10 minutes and transplantation of the non-cellular root canal filling material in which regeneration promoting compounds (CCR3 antagonist, ALK5 inhibitor) is mixed with atelocollagen and the migration factor G-CSF. B and D illustrate regenerated tissue after transplantation of the cellular root canal filling material in which allogeneic dental pulp stem cells (MDPSCs) and G-CSF are mixed with atelocollagen without pretreatment.

28 days after the injection of a non-cellular root canal filling material containing regeneration promoting compounds (an ALK5 inhibitor and a CCR3 antagonist) and the migration factor G-CSF into root canals after pulpectomy of teeth in middle-aged dogs after trypsin pretreatment, no inflammatory cell infiltration or internal absorption was observed, but regeneration of dental pulp-like tissues which were loose connective tissue rich in blood vessels similar to injection of a cellular root canal filling material containing allogeneic membrane-fractionated dental pulp stem cells and G-CSF with no trypsin pretreatment according to a conventional method was observed (FIG. 1 A to D). Moreover, it was observed in both methods that odontoblast-like cells were attached to the dentin sidewalk to form dentin (FIGS. 1 C, D). No statistically significant difference was found in the amount of dental pulp regeneration (FIG. 1 E). When a non-cellular dental tissue regeneration promoting kit was used, the angiogenesis (FIGS. 2 A, B) and the neurite extension (FIGS. 2 C, D) were observed, as seen when a cellular root canal filling material was used. 28 days later, no significant difference between the amount of the angiogenesis when the non-cellular dental tissue regeneration promoting kit was used and the amount of the angiogenesis when the conventional cellular root canal filling material was used was found (FIG. 2 E). Also, 28 days later, no significant difference between the amounts of the neurite extension in both cases was found (FIG. 2 F). Furthermore, in the tissue regenerated when the non-cellular dental tissue regeneration promoting kit was used, some cells were found to be TRH-DE-positive cells, as seen in the tissue when the conventional cellular root canal filling material was used (FIGS. 3 A, B). Moreover, in the dentin wall, cells expressing enamelysin mRNA were found (FIGS. 3 C, D).

From these results, it was revealed that injection of a non-cellular root canal filling material containing regeneration promoting compounds (an ALK5 inhibitor and a CCR3 antagonist) and the migration factor G-CSF after trypsin pretreatment results in the dental pulp regeneration with angiogenesis and neurite extension and the formation of dentin-like hard tissue is on dentin sidewalls, similar to the dental pulp regeneration by conventional dental pulp stem cells and G-CSF transplantation.

Example 2

Dental Pulp Regeneration After Pulpectomy in Young Dogs by Non-Cellular Dental Tissue Regeneration Promoting Kit After giving general anesthesia, pulpectomy of maxillary and mandibular right and left anterior teeth in young (8-month-old) dogs was performed. The opening was enlarged to the apical area with #55, then washed alternately with 5% sodium hypochlorite solution and with 3% hydrogen peroxide solution, and further washed with saline. The root canals were completely dried with a paper point and temporarily sealed with cement and resin completely after stopping the bleeding. 3 days after the pulpectomy, the temporary seals were removed and the openings were rewashed alternately and washed with saline. The root canals were then treated with 3% EDTA (Smear clean) for 2 minutes, further washed with saline, and dried. Subsequently, the root canals were treated with a 5 mg/nil (0.5%, dissolved in nanobubble water) trypsin preparation (Francetin T powder (2,500 USP crystal trypsin per 10 mg)) for 10 minutes to be pretreated and washed with saline. Furthermore, the right maxillary and mandibular root canals were filled with a non-cellular root canal filling material comprising a CCR3 antagonist ((SB328437, 200 ng) and an ALK5 inhibitor (SB431542, 200 ng) as regeneration promoting compounds and 20 µl of the extracellular matrix collagen (Koken atelocollagen implant). Meanwhile, the left maxillary and mandibular root canals were filled with a non-cellular root canal filling material comprising a CCR3 antagonist ((SB328437, 200 ng) as a regeneration promoting compound and 20 µl of the extracellular matrix collagen (Koken atelocollagen implant). Subsequently, a gelatin sponge (Spongel) for hemostasis was placed thereon and the cavities were completely sealed with a glass ionomer cement and a photo-polymerized resin. Then, 13 days after the transplantation, the teeth were extracted and 5 µm paraffin pieces on longitudinal sections were prepared according to a usual method and the morphology was observed after the H-E staining. The angiogenesis and the neurite extension were examined by comparison of immunostaining respectively with BS-1 lectin and with PGP9.5. Furthermore, immunostaining of TRH-DE and in situ hybridization of enamelysin of Day 13 specimens were performed.

Figure 4:
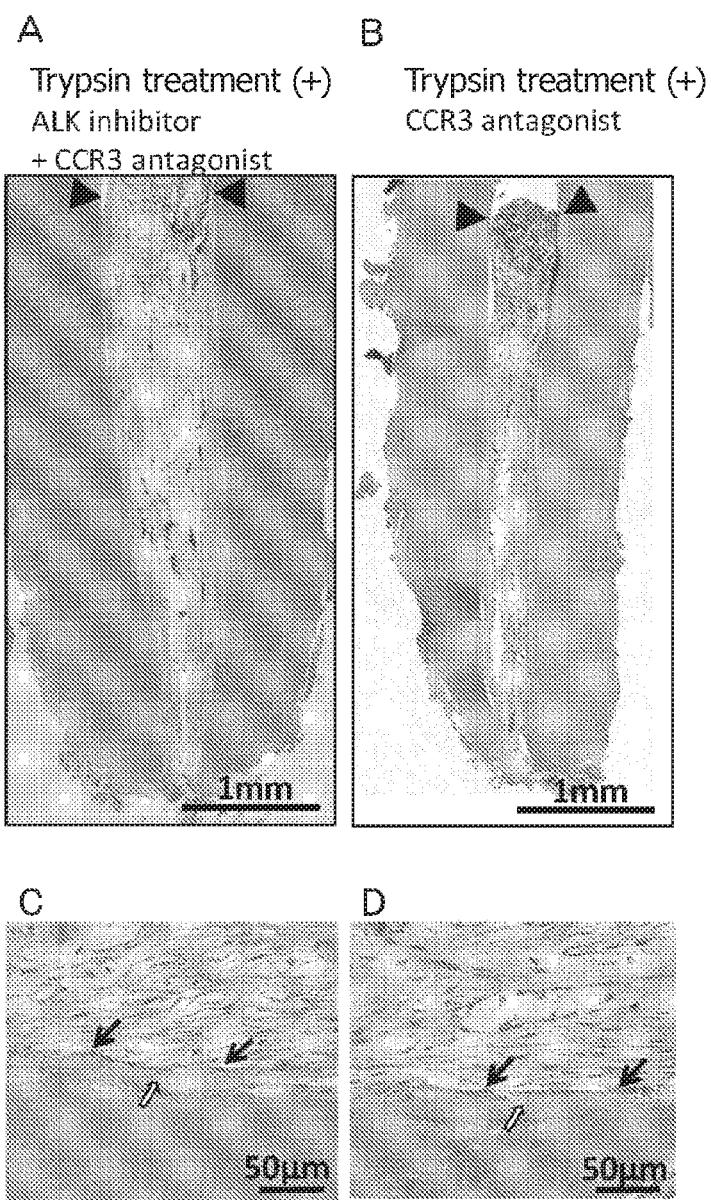
FIG. 4 is a set of photographs of H-E staining on Day 13 after transplantation illustrating the comparison of regenerated dental pulp tissue with a non-cellular root canal filling material between with and without an ALK5 inhibitor, a regeneration promoting compound in 8-month-old dogs. A and B are at low magnification and the arrow heads indicate the top of regenerated tissue. C and D are at high magnification and the black arrows indicate odontoblast-like cells and the white arrows indicate the formation of dentin-like hard tissue. Among them, A and C illustrate regenerated dental pulp tissue after treatment with a pretreatment agent comprising trypsin for 10 minutes and transplantation of a non-cellular root canal filling material in which a CCR3 antagonist and an ALK5 inhibitor, which are regeneration promoting compounds, are mixed with atelocollagen. B and D illustrate regenerated tissue after treatment with a pretreatment agent comprising trypsin for 10 minutes and transplantation of a non-cellular root canal filling material in which only a CCR3 antagonist is mixed with atelocollagen.
Figure 5:
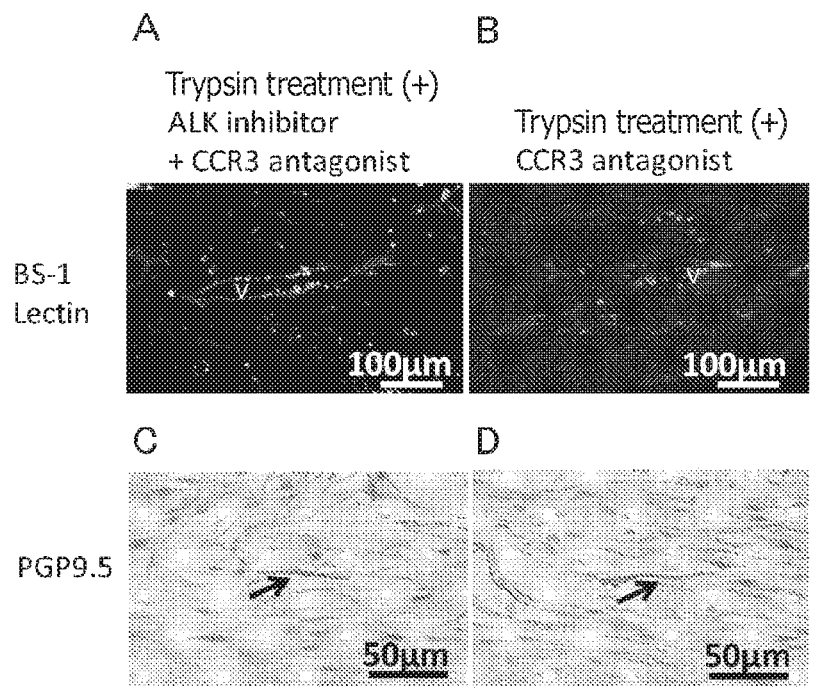
FIG. 5 is a set of photographs on Day 13 after transplantation illustrating the comparison of angiogenesis and neurite extension in regenerated tissue with a non-cellular root canal filling material between with and without an ALK5 inhibitor, a regeneration promoting compound in 8-month-old dogs. A and B illustrate angiogenesis (BS-1 lectin staining) and V indicates neovessels. C and D illustrate the neurite extension (PGP9.5 staining) and the arrows indicate neurites. Among them, A and C illustrate regenerated dental pulp tissue after treatment with a pretreatment agent comprising trypsin for 10 minutes and transplantation of the non-cellular root canal filling material in which a CCR3 antagonist and an ALK5 inhibitor, which are regeneration promoting compounds, are mixed with atelocollagen. B and D illustrate regenerated tissue after treatment with a pretreatment agent comprising trypsin for 10 minutes and transplantation of a non-cellular root canal filling material in which only a CCR3 antagonist, a regeneration promoting compound, is mixed with atelocollagen.
Figure 6:
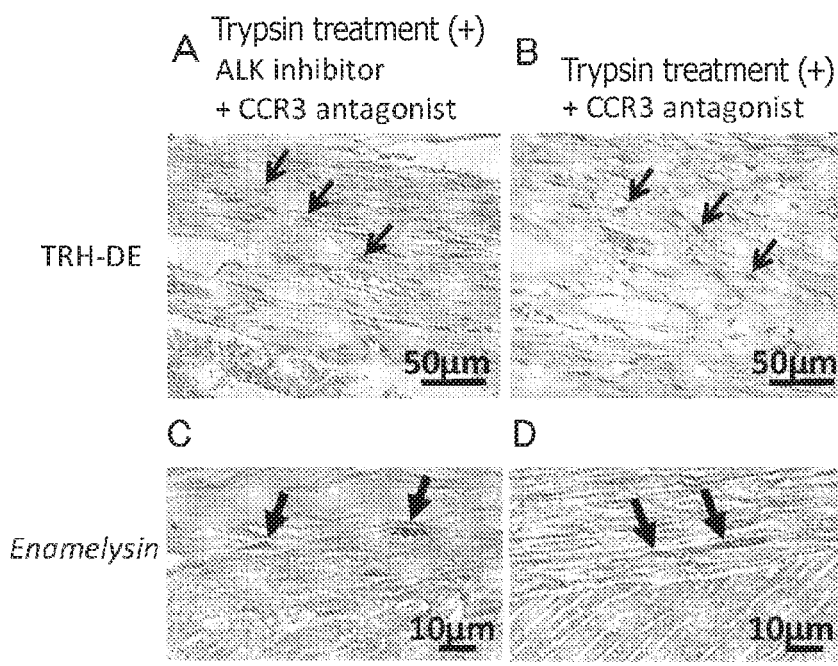
FIG. 6 is a set of photographs of regenerated tissue on Day 13 after transplantation illustrating comparison with and without an ALK5 inhibitor, a regeneration promoting compound using dental pulp and odontoblast markers in regenerated tissue with a non-cellular root canal filling material in 8-month-old dogs. A and B illustrate a dental pulp marker (TRH-DE immunostaining) and the arrows indicate positive cells. C and D illustrate in situ hybridization of the odontoblast marker Enamelysin mRNA and the arrows indicate positive cells. Among them, A and C illustrate regenerated dental pulp tissue after treatment with a pretreatment agent comprising trypsin for 10 minutes and transplantation of the non-cellular root canal filling material in which a CCR3 antagonist and an ALK5 inhibitor, which are regeneration promoting compounds, are mixed with atelocollagen. B and D illustrate regenerated tissue after treatment with a pretreatment agent comprising trypsin for 10 minutes and transplantation of a non-cellular root canal filling material in which only a CCR3 antagonist is mixed with atelocollagen.

Then, 13 days after injection of the non-cellular root canal filling material containing the ALK5 inhibitor and the CCR3 antagonist and collagen into the root canals after the pulpectomy of teeth in young dogs, after trypsin pretreatment, no inflammatory cell infiltration or internal absorption was observed, but dental pulp regeneration of loose connective tissue rich in blood vessels was observed (FIGS. 4 A, C). Moreover, after injection of a non-cellular root canal filling material containing the CCR3 antagonist and collagen after trypsin pretreatment, regeneration of dental pulp tissue was similarly observed while the amount of regeneration observed had a tendency to slightly decrease in comparison with a root canal filling material containing both of the ALK5 inhibitor and the CCR3 antagonist (FIGS. 4 B, D). Moreover, it was observed in both cases that odontoblast-like cells were attached to the dentin sidewalls to form dentin (FIGS. 4 C, D). Moreover, the angiogenesis (FIGS. 5 A, B) and the neurite extension (FIGS. 5 C, D) were similarly observed in both cases. In the regenerated tissue by both non-cellular dental tissue regeneration promoting kits, some cells were similarly found to be TRH-DE-positive cells (FIGS. 6 A, B). Moreover, in the dentin wall, cells expressing enamelysin mRNA were similarly found (FIGS. 6 C, D).

From these results, it was revealed that injection of a non-cellular root canal filling material containing a CCR3 antagonist and collagen after trypsin pretreatment results in the regeneration of dental pulp with angiogenesis and neurite extension and the attachment of odontoblast-like cells to the dentin sidewalls and formation of dentin-like hard tissue, approximately similar to those seen with a non-cellular root canal filling material containing an ALK5 inhibitor and a CCR3 antagonist and collagen.

Example 3

Comparison of Dental Pulp Regeneration After Pulpectomy in Young Dogs by Non-Cellular Dental Tissue Regeneration Promoting Kits Containing Migration Factor bFGF or G-CSF After giving general anesthesia, pulpectomy of maxillary and mandibular right and left anterior teeth in young (8-month-old) dogs was performed. The openings were enlarged to the apical area with #55, then washed alternately with 5% sodium hypochlorite solution and with 3% hydrogen peroxide solution, and further washed with saline. The root canals were completely dried with a paper point and the bleeding was stopped. The root canals were then treated with 3% EDTA (Smear clean) for 2 minutes, further washed with saline, and dried. After this, the root canals were wetted with a 5 mg/ml (0.5%, dissolved in nanobubble water) trypsin preparation (Francetin T powder (2,500 USP crystal trypsin per 10 mg), Mochida Pharmaceutical Co., Ltd.) for 10 minutes to be pretreated and washed with saline. Furthermore, the right maxillary and mandibular root canals were filled with a non-cellular root canal filling material comprising a CCR3 antagonist ((SB328437, 200 ng) and an ALK5 inhibitor (SB431542, 200 ng) as regeneration promoting compounds, 150 ng of bFGF (Fiblast Spray, Kaken Pharmaceutical Co., Ltd.) as a migration factor, and 20 µl of the extracellular matrix collagen (Koken atelocollagen implant). Meanwhile, the left maxillary and mandibular root canals were filled with a non-cellular root canal filling material comprising a CCR3 antagonist ((SB328437, 200 ng) and an ALK5 inhibitor (SB431542, 200 ng) as regeneration promoting compounds, 150 ng of G-CSF (Neutrogin) as a migration factor, and 20 µl of the extracellular matrix collagen (Koken atelocollagen implant). Subsequently, a gelatin sponge (Spongel) for hemostasis was placed thereon and the cavities were completely sealed with a glass ionomer cement and a photo-polymerized resin. Then, 13 days after the transplantation, the teeth were extracted and 5 µm paraffin pieces on longitudinal sections were prepared according to a usual method and the morphology was observed after the H-E staining. The angiogenesis and the neurite extension were examined by comparison of immunostaining respectively with BS-1 lectin and with PGP9.5. Furthermore, the immunostaining of TRH-DE and in situ hybridization of enamelysin of Day 13 specimens were performed.

Figure 7:
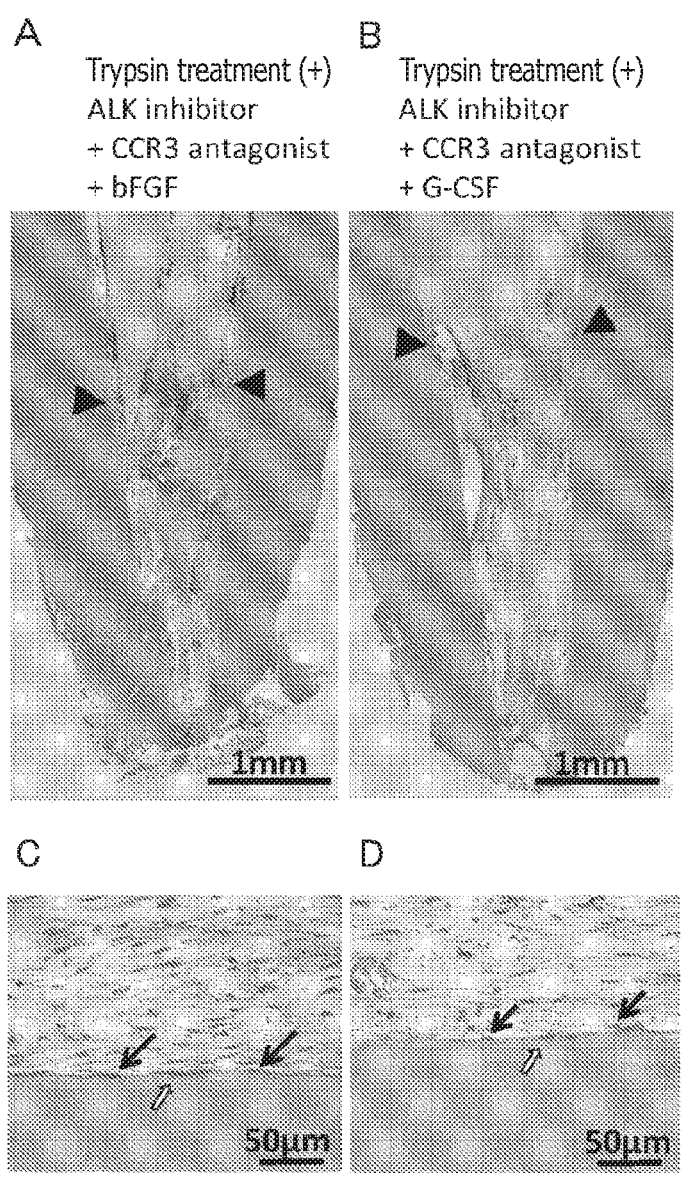
FIG. 7 is a set of photographs of H-E staining on Day 13 after transplantation illustrating the comparison of regenerated dental pulp tissue by a non-cellular dental tissue regeneration promoting kit to which a migration factor, bFGF or G-CSF, is added in 8-month-old dogs. A and B are at low magnification and the arrow heads indicate the top of regenerated tissue. C and D are at high magnification and the black arrows indicate odontoblast-like cells and the white arrows indicate the formation of dentin-like hard tissue. Among them, A and C illustrate regenerated tissue after treatment with a pretreatment agent comprising trypsin for 10 minutes and transplantation of the non-cellular root canal filling material in which a CCR3 antagonist and an ALK5 inhibitor, which are regeneration promoting compounds, and the migration factor bFGF are mixed with atelocollagen. B and D illustrate regenerated tissue after treatment with a pretreatment agent comprising trypsin for 10 minutes and transplantation of the non-cellular root canal filling material in which a CCR3 antagonist and an ALK5 inhibitor, which are regeneration promoting compounds, and the migration factor G-CSF are mixed with atelocollagen.
Figure 8:
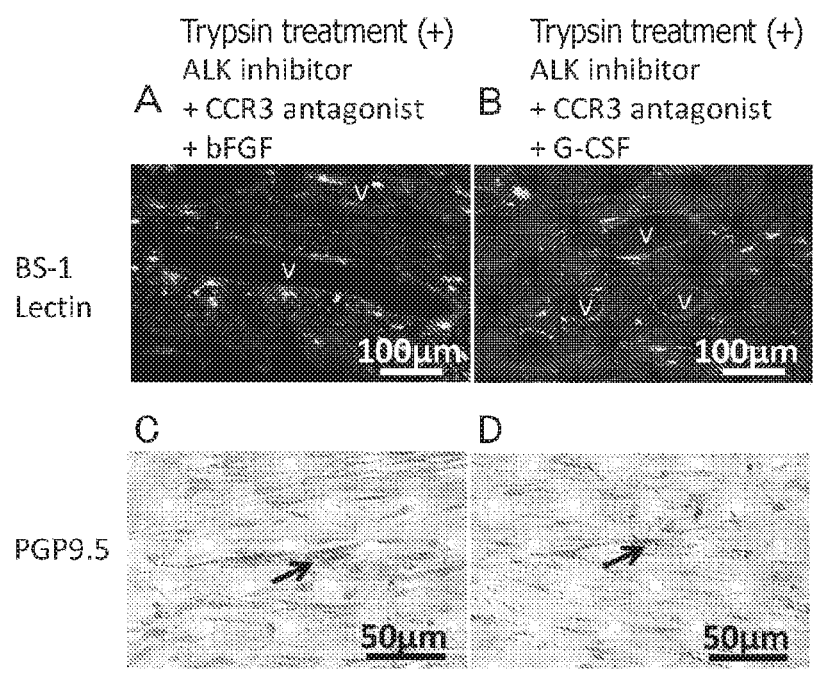
FIG. 8 is a set of photographs on Day 13 after transplantation illustrating the comparison of angiogenesis and neurite extension in regenerated dental pulp tissue by a non-cellular dental tissue regeneration promoting kit to which a migration factor, bFGF or G-CSF, is added in 8-month-old dogs. A and B illustrate angiogenesis (BS-1 lectin staining) and V indicates neovessels. C and D illustrate the neurite extension (PGP9.5 staining) and the arrows indicate neurites. Among them, A and C illustrate regenerated tissue after treatment with a pretreatment agent comprising trypsin for 10 minutes and transplantation of the non-cellular root canal filling material in which a CCR3 antagonist and an ALK5 inhibitor, which are regeneration promoting compounds, and the migration factor bFGF are mixed with atelocollagen. B and D illustrate regenerated tissue after treatment with a pretreatment agent comprising trypsin for 10 minutes and transplantation of the non-cellular root canal filling material in which a CCR3 antagonist and an ALK5 inhibitor, which are regeneration promoting compounds, and the migration factor G-CSF are mixed with atelocollagen.
Figure 9:
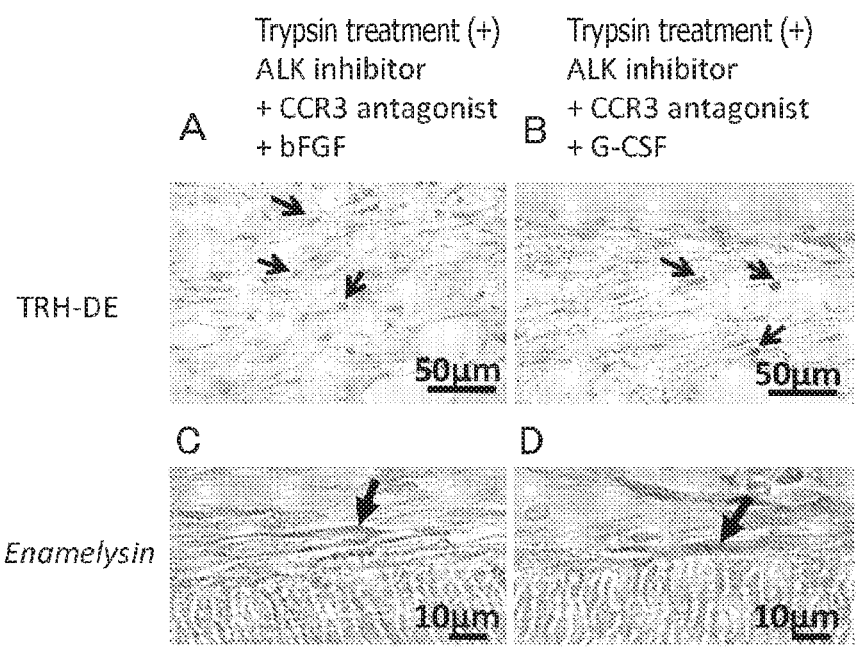
FIG. 9 is a set of photographs on Day 13 after transplantation using dental pulp and odontoblast markers in regenerated dental pulp tissue by a non-cellular dental tissue regeneration promoting kit to which a migration factor, bFGF or G-CSF, is added in 8-month-old dogs. A and B illustrate a dental pulp marker (TRH-DE immunostaining) and the arrows indicate positive cells. C and D illustrate in situ hybridization of the odontoblast marker Enamelysin mRNA. Among them, A and C illustrate regenerated tissue after treatment with a pretreatment agent comprising trypsin for 10 minutes and transplantation of the non-cellular root canal filling material in which a CCR3 antagonist and an ALK5 inhibitor, which are regeneration promoting compounds, and the migration factor bFGF are mixed with atelocollagen. B and D illustrate regenerated tissue after treatment with a pretreatment agent comprising trypsin for 10 minutes and transplantation of the non-cellular root canal filling material in which a CCR3 antagonist and an ALK5 inhibitor, which are regeneration promoting compounds, and the migration factor G-CSF are mixed with atelocollagen.

13 days after injection of the non-cellular root canal filling material containing the ALK5 inhibitor and the CCR3 antagonist, bFGF, and collagen into the root canals after pulpectomy of the teeth in young dogs after trypsin pretreatment, regeneration of dental pulp-like tissue with neovessels similar to that seen with a non-cellular root canal filling material containing G-CSF was observed, while the amount of dental pulp regeneration observed had a tendency to slightly decrease (FIG. 7 A to D). Moreover, it was observed in both cases that odontoblast-like cells were attached to the dentin sidewalls to form dentin (FIGS. 7 C, D). The dentin formation tended to be slightly higher with G-CSF. Furthermore, the angiogenesis (FIGS. 8 A, B) and the neurite extension (FIGS. 8 C, D) were similarly observed in both cases. In the regeneration tissue with a root canal filling material in both cases, some cells were similarly found to be TRH-DE-positive cells (FIGS. 9 A, B). Moreover, in the dentin wall, cells expressing enamelysin mRNA were similarly found (FIGS. 9 C, D).

From these results, it was revealed that the injection of a non-cellular root canal filling material containing the ALK5 inhibitor and the CCR3 antagonist and collagen and bFGF or G-CSF as a migration factor after trypsin pretreatment gave approximately similarly results in the regeneration of dental pulp with angiogenesis and nerve elongation and the formation of dentin-like hard tissue on the dentin sidewalls.

Example 4

Comparison of Dental Pulp Regeneration After Pulpectomy in Middle-Aged Dogs with Non-Cellular Root Canal Filling Material in the Presence or Absence of Trypsin Pretreatment After giving general anesthesia, the pulpectomy of maxillary right and left central incisors in middle-aged (2-year-old) dogs was performed. The opening was enlarged to the apical area with #50, then washed alternately with 5% sodium hypochlorite solution and with 3% hydrogen peroxide solution, and further washed with saline. The root canals were completely dried with a paper point and temporarily sealed with cement and resin completely after stopping the bleeding. After pulpectomy, the temporary seals were removed and the openings were rewashed alternately and washed with saline. The root canals were then treated with 3% EDTA (Smear clean) for 2 minutes, further washed with saline, and dried. Subsequently, the right root canal was wetted with a 5 mg/ml (0.5%) trypsin preparation (Francetin T powder (2,500 USP crystal trypsin per 10 mg)) for 10 minutes to be pretreated and treated with saline. Meanwhile, the left root canal was not treated by trypsin pretreatment. Furthermore, all root canals were filled with a non-cellular root canal filling material containing an ALK5 inhibitor (SB431542, 200 ng) and a CCR3 antagonist (SB328437, 200 ng), 20 µl of the extracellular matrix collagen (Koken atelocollagen implant), and G-CSF (Neutrogin, 150 ng) as a migration factor. Subsequently, a gelatin sponge (Spongel) for hemostasis was placed thereon and the cavities were completely sealed with a glass ionomer cement and a photo-polymerized resin. The teeth were extracted 28 days after the transplantation. Then, 5 µm paraffin pieces on longitudinal sections were prepared according to a usual method and the morphology was observed after the H-E staining. The angiogenesis and the neurite extension were examined by comparison of immunostaining respectively with BS-1 lectin and with PGP9.5. Furthermore, the immunostaining of TRH-DE and in situ hybridization of enamelysin of Day 28 specimens were performed.

Figure 10:
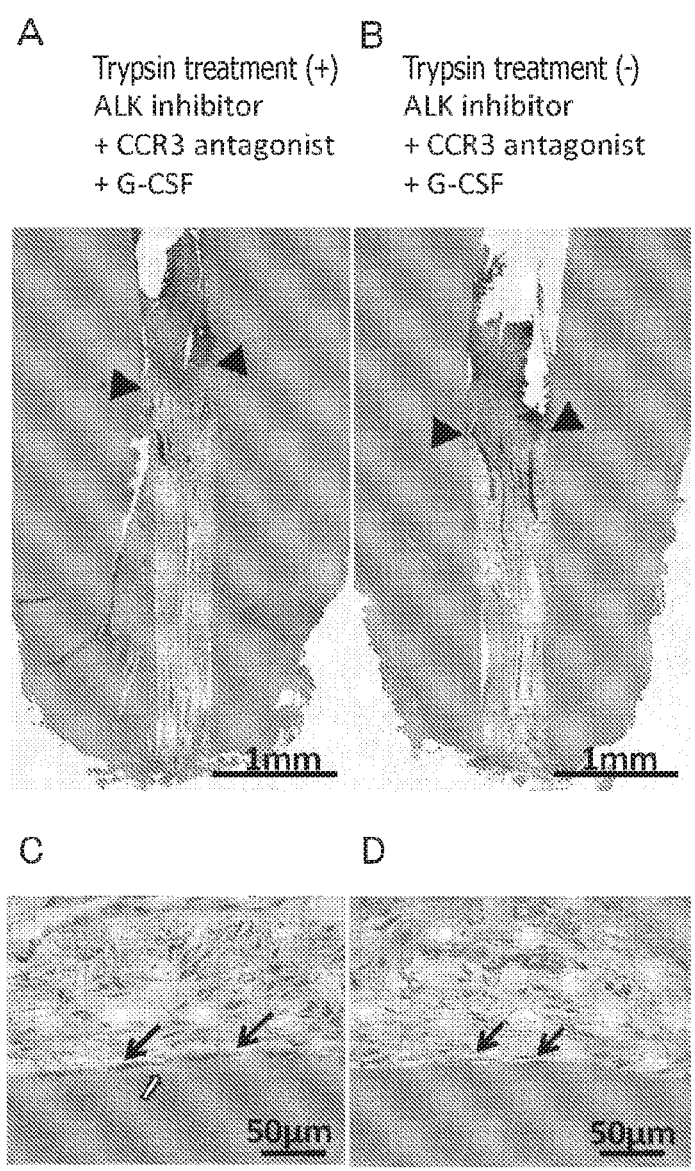
FIG. 10 is a set of photographs of H-E staining on Day 28 after transplantation illustrating the comparison of regenerated dental pulp tissue with a non-cellular root canal filling material between with and without trypsin pretreatment in 2-year-old dogs. A and B are at low magnification and the arrow heads indicate the top of regenerated tissue. C and D are at high magnification and the black arrows indicate odontoblast-like cells and the white arrows indicate the formation of dentin-like hard tissue. Among them, A and C illustrate regenerated tissue after treatment with a pretreatment agent comprising trypsin for 10 minutes and transplantation of the non-cellular root canal filling material in which a CCR3 antagonist and an ALK5 inhibitor, which are regeneration promoting compounds, and the migration factor G-CSF are mixed with atelocollagen. B and D illustrate regenerated tissue after transplantation of the non-cellular root canal filling material in which a CCR3 antagonist and an ALK5 inhibitor, which are regeneration promoting compounds, and the migration factor G-CSF are mixed with atelocollagen, without trypsin pretreatment.
Figure 11:
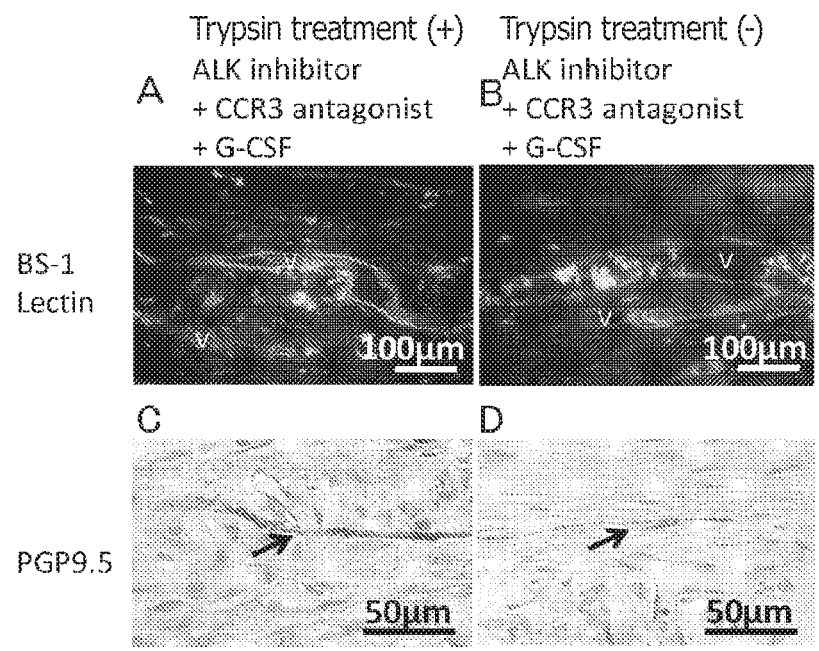
FIG. 11 is a set of photographs on Day 28 after transplantation illustrating the comparison of angiogenesis and neurite extension in regenerated dental pulp tissue with a non-cellular root canal filling material between with and without trypsin pretreatment in 2-year-old dogs. A and B illustrate angiogenesis (BS-1 lectin staining). C and D illustrate the neurite extension (PGP9.5 staining) and the arrows indicate neurites. Among them, A and C illustrate regenerated dental pulp tissue after treatment with a pretreatment agent comprising trypsin for 10 minutes and transplantation of the non-cellular root canal filling material in which a CCR3 antagonist and an ALK5 inhibitor, which are regeneration promoting compounds, and the migration factor G-CSF are mixed with atelocollagen. B and D illustrate regenerated dental pulp tissue after transplantation of the non-cellular root canal filling material in which a CCR3 antagonist and an ALK5 inhibitor, which are regeneration promoting compounds, and the migration factor G-CSF are mixed with atelocollagen, without trypsin pretreatment.
Figure 12:
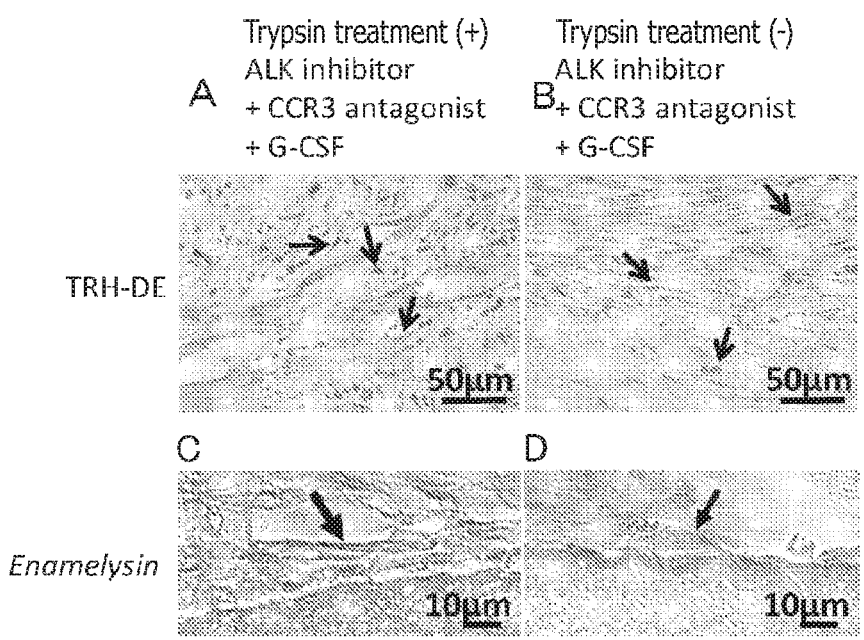
FIG. 12 is a set of photographs of regenerated tissue on Day 28 after transplantation using dental pulp and odontoblast markers in regenerated dental pulp tissue with the non-cellular root canal filling material between with and without trypsin pretreatment in 2-year-old dogs. A and B illustrate a dental pulp marker (TRH-DE immunostaining) and the arrows indicate positive cells. C and D illustrate in situ hybridization of the odontoblast marker Enamelysin mRNA. Among them, A and C illustrate regenerated dental pulp tissue after treatment with a pretreatment agent comprising trypsin for 10 minutes and transplantation of the non-cellular root canal filling material in which a CCR3 antagonist and an ALK5 inhibitor, which are regeneration promoting compounds, and the migration factor G-CSF are mixed with atelocollagen. B and D illustrate regenerated dental pulp tissue after transplantation of the non-cellular root canal filling material in which a CCR3 antagonist and an ALK5 inhibitor, which are regeneration promoting compounds, and the migration factor G-CSF are mixed with atelocollagen, without trypsin pretreatment.

Then, 28 days after injection of the non-cellular root canal filling material containing the ALK5 inhibitor and the CCR3 antagonist, collagen, and G-CSF into the root canals after pulpectomy of the teeth in middle-aged dogs after trypsin pretreatment, regeneration of dental pulp tissue was observed approximately similar to that seen with no trypsin pretreatment, but the amount of dental pulp regeneration had a tendency to slightly increase with trypsin pretreatment (FIG. 10 A to D). Moreover, when trypsin pretreatment was performed, more odontoblast-like cells attached to the dentin sidewalls and the amount of dentin-like hard tissue formation also had a tendency to be slightly higher (FIGS. 10 C, D). Furthermore, the angiogenesis (FIGS. 11 A, B) and the neurite extension (FIGS. 11 C, D) were similarly observed in both cases. In the tissue regenerated with a root canal filling material in both cases, some cells were similarly found to be TRH-DE-positive cells (FIGS. 12 A, B). Moreover, in the dentin wall, cells expressing enamelysin mRNA were similarly found (FIGS. 12 C, D).

From these results, it was revealed that injection of a non-cellular root canal filling material containing an ALK5 inhibitor and a CCR3 antagonist, collagen, and G-CSF results in regeneration of dental pulp with angiogenesis and neurite extension, but injection of a non-cellular root canal filling material as a non-cellular dental tissue regeneration promoting kit after trypsin pretreatment results in the attachment of more cells to the dentin sidewalls and the promotion of differentiation into odontoblasts and formation of dentin-like tissue.

Example 5

Analysis of Human Dental Pulp Stem Cell Culture and CCL11 and CCR3 mRNA Expression After obtaining consent, dental pulp was removed from third molars of elderly (60-year-old and 70-year-old) persons and young (19-year-old and 26-year-old) persons, sliced in Hanks' solution, and then enzymatically digested with 0.04 mg/ml Liberase solution (Roche diagnostics, Pleasanton, CA, USA) at 37° C. for 1 hour to separate pulp cells. The cells were seeded at a cell concentration of 2 to $4 \times 10^4$/ml into DMEM (D6429) (Sigma-Aldrich, St. Louis, MO, USA) containing 10% human serum in a 35 mm dish. Afterward, the medium was refreshed every 2 to 3 days and subcultured at a confluency of 70%. For detachment of cells, TrypLE(R) Select (Life Technologies, Carlsbad, CA, USA) was used.

Total RNA was extracted from each type of cells using Trizol (Life Technologies) and treated with DNase (Roche diagnostics) and first-strand cDNA was synthesized with ReverTra Ace-a (TOYOBO, Tokyo, Japan). For real-time RT-PCR, the CCL11 mRNA was amplified and detected using PowerUp (R) SYBR (R) Green master mix (Applied Biosystems, Foster City, CA, USA) and the b-actin and CCR3 mRNAs were amplified and detected using Power SYBR (R) Green master mix (Applied Biosystems) in Applied Biosystems 7500 Real-time PCR system (Applied Biosystems). The reaction conditions for Real-time RT-PCR were 40 cycles of 95° C. for 15 seconds and 65° C. for 1 minute. The nucleotide sequences of the primers used are set forth in Table 1. The mRNA expression of the amplified genes was corrected with b-actin mRNA.

TABLE 1

| Gene | | 5'←DNA Sequence→3' | Product size | Accession number |
|---|---|---|---|---|
| β-actin | Forward 5'-1 | GGACTTCGAGCAAGAGATGG | 234 bp | NM_001101 |
| | Reverse 3'-2 | AGCACTGTGTTGGCGTACAG | | |
| CCL11 | Forward 5'-3 | TTCTGTGGCTGCTGCTCATAG | 125 bp | NM_002986 |
| | Reverse 3'-6 | GCTCTCTAGTCGCTGAAGGG | | |
| CCR3 | Forward 5'-1 | CTGTACTCCCTGGTGTTCACTG | 109 bp | Nm_001837 |
| | Reverse 3'-2 | GGTTGAGCAGGTAGATGTTGG | | |

Figure 13:
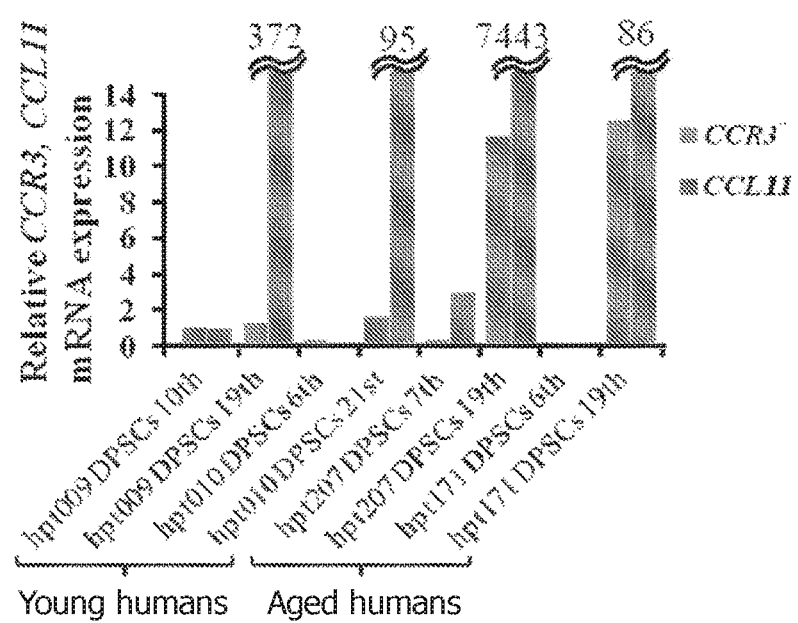
FIG. 13 illustrates CCL11 and CCR3 mRNA expression in each lot of dental pulp stem cells (DPSCs) derived from young and aged humans.

Dental pulp stem cells in both young and elderly humans had a tendency for very low CCR3 mRNA expression and no or low CCL11 mRNA expression during small passage numbers (6 to 10 generations). Moreover, increased expression of CCL11 mRNA and CCR3 mRNA was found during large passage numbers (19 to 21 generations) in both young and elderly humans (FIG. 13). Meanwhile, it has been reported that the CCL11 sensitivity is increased by increased expression of CCR3, a CCL11 receptor, in cells derived from elderly individuals (Wang H et al. Invest Ophthalmol Vis Sci. 2011). In other words, the possibility that the correlation between the expression of CCL11 and the expression of CCR3, a CCL11 receptor, is increased particularly with age has been suggested.

Therefore, it is suggested that CCL11 neutralizing antibodies, which bind to CCL11, and CCR3 antagonists, which bind to CCR3, a CCL11 receptor, have the approximately similar effect in the dental pulp regeneration using a non-cellular root canal filling material.

INDUSTRIAL APPLICABILITY

The present invention is applicable to dental tissue regeneration.

SEQUENCE LISTING FREE TEXT

SEQ ID NOs: 1-6: primers

The invention claimed is:

1. A non-cellular root canal filling material comprising: a regeneration promoting compound including at least one of a CCR3 antagonist, a CCL11 neutralizing antibody, and an ALK5 inhibitor; and an extracellular matrix.

2. The non-cellular root canal filling material according to claim 1, wherein the non-cellular root canal filling material comprises: regeneration promoting compounds including the CCR3 antagonist and the ALK5 inhibitor; and the extracellular matrix.

3. The non-cellular root canal filling material according to claim 1, wherein the non-cellular root canal filling material comprises a migration factor including at least one of G-CSF, bFGF, and SDF-1.

4. The non-cellular root canal filling material according to claim 1, wherein the non-cellular root canal filling material is used for a young individual.

5. A non-cellular dental tissue regeneration promoting kit, comprising:
a pretreatment agent comprising a serine protease; and
a non-cellular root canal filling material comprising: a regeneration promoting compound including at least one of a CCR3 antagonist, a CCL11 neutralizing antibody, and an ALK5 inhibitor; and an extracellular matrix.

6. The non-cellular dental tissue regeneration promoting kit according to claim 5, wherein the non-cellular dental tissue regeneration promoting kit comprises:
the pretreatment agent comprising the serine protease; and
a non-cellular root canal filling material, the non-cellular root canal filling material comprising: regeneration promoting compounds including the CCR3 antagonist or the CCL11 neutralizing antibody, and the ALK5 inhibitor; and the extracellular matrix.

7. The non-cellular dental tissue regeneration promoting kit according to claim 5, wherein the non-cellular root canal filling material comprises a migration factor including at least one of G-CSF, bFGF, and SDF-1.

8. The non-cellular dental tissue regeneration promoting kit according to claim 5, wherein the non-cellular dental tissue regeneration promoting kit is used for a middle-aged or elderly individual.

9. The non-cellular dental tissue regeneration promoting kit according to claim 5, wherein the serine protease is a chymotrypsin-like serine protease.

10. The non-cellular dental tissue regeneration promoting kit according to claim 9, wherein the chymotrypsin-like serine protease is trypsin.

* * * * *

UNITED STATES PATENT AND TRADEMARK OFFICE
CERTIFICATE OF CORRECTION

PATENT NO. : 11,969,487 B2
APPLICATION NO. : 16/651483
DATED : April 30, 2024
INVENTOR(S) : Nakashima et al.

It is certified that error appears in the above-identified patent and that said Letters Patent is hereby corrected as shown below:

In the Specification

Column 2, Line 35: Please correct "(Patent" to read --(Non-Patent--

Column 15, Line 57: Please correct "5 mg/nil" to read --5 mg/ml--

Column 20, Table 1 – continued: Please correct "Nm_001837" to read --NM_001837--

Signed and Sealed this
Thirtieth Day of July, 2024

Katherine Kelly Vidal
*Director of the United States Patent and Trademark Office*